United States Patent
Rusznak et al.

(10) Patent No.: US 10,226,409 B2
(45) Date of Patent: Mar. 12, 2019

(54) PYRUVATE AND RELATED α-KETO CARBOXYLATES AS NOVEL ADJUVANTS IN THE TREATMENT OF POST TOOTH WHITENING SENSITIVITY AND THE TISSUE PROTECTIVE EFFECT OF PYRUVATE ON THE ORAL SOFT TISSUE

(71) Applicants: Zoltan Rusznak, Ashburn, VA (US); Rolf Bunger, McLean, VA (US)

(72) Inventors: Zoltan Rusznak, Ashburn, VA (US); Rolf Bunger, McLean, VA (US)

( * ) Notice: Subject to any disclaimer, the term of this patent is extended or adjusted under 35 U.S.C. 154(b) by 0 days.

(21) Appl. No.: 15/712,617

(22) Filed: Sep. 22, 2017

(65) Prior Publication Data

US 2018/0369090 A1    Dec. 27, 2018

Related U.S. Application Data

(63) Continuation of application No. 15/051,647, filed on Feb. 23, 2016, now abandoned.

(51) Int. Cl.
| | |
|---|---|
| *A61K 8/22* | (2006.01) |
| *A61K 31/19* | (2006.01) |
| *A61K 8/365* | (2006.01) |
| *A61Q 11/00* | (2006.01) |

(52) U.S. Cl.
CPC ............... *A61K 8/365* (2013.01); *A61K 8/22* (2013.01); *A61K 31/19* (2013.01); *A61Q 11/00* (2013.01); *A61K 2800/882* (2013.01)

(58) Field of Classification Search
CPC ........ A61K 31/19; A61K 31/185; A01N 1/02; A01N 59/00; A01N 63/00
USPC .................. 422/29; 424/10.32, 401; 433/215
See application file for complete search history.

(56) References Cited

U.S. PATENT DOCUMENTS

| | | | | |
|---|---|---|---|---|
| 4,521,375 A | * | 6/1985 | Houlsby | A01N 59/00 134/27 |
| 5,055,287 A | * | 10/1991 | Kessler | A01N 63/00 424/10.32 |
| 5,536,751 A | * | 7/1996 | Bunger | A61K 31/19 514/557 |

OTHER PUBLICATIONS

Rolf Bunger et al., Redox and Antioxidant Mechanisms of Pyruvate in Cellular Oxidative Stress: Enhanced Survival Signaling and Mitochondrial Stability. In: Recent Res. Devel. Physiol. 4, 1-25, 2006. Publisher: Research Signpost, 37/661(2) Fort P.O., Trivandrum-695 023, Kerala, India.

* cited by examiner

*Primary Examiner* — Walter E Webb

(74) *Attorney, Agent, or Firm* — Bernard G. Pike; Pike IP Law, PLLC

(57) ABSTRACT

This invention describes pyruvate and related α-ketocarboxylates as novel adjuvants in the treatment of acute post-tooth-whitening pain and sensitivity; the key feature is the cytoprotective efficacy of pyruvate on oral soft tissue, especially after topical application of high and therefore cytotoxic concentrations of $H_2O_2$, currently used in tooth whitening procedures.

4 Claims, No Drawings

PYRUVATE AND RELATED α-KETO CARBOXYLATES AS NOVEL ADJUVANTS IN THE TREATMENT OF POST TOOTH WHITENING SENSITIVITY AND THE TISSUE PROTECTIVE EFFECT OF PYRUVATE ON THE ORAL SOFT TISSUE

RELATED APPLICATIONS

This application is a continuation application filed under 35 U.S.C. 120 claiming priority to U.S. patent application Ser. No. 15/051,647 having a filing date of Feb. 23, 2016 and is hereby incorporated by reference in its entirety.

I. TECHNICAL FIELD OF THE INVENTION

The invention is in the field of protecting, preserving and restoring normal cell functions. More specifically it is in the field of using alpha-keto carboxylic acid salt compositions as prophylactic and therapeutic agents to prevent the deterioration or promote the restoration and preservation of normal cell functions in the oral cavity.

II. BACKGROUND OF THE INVENTION

Hydrogen peroxide ($H_2O_2$), carbamide peroxide (CP) and peroxo-adducts of inorganic anions such as peroxoborate, peroxodisulphate and peroxocarbonate as agents for the bleaching of discolored teeth in professional and commercially-available tooth-whitening products such as gels, toothpastes and oral rinses has created much interest regarding their mechanisms of action and redox activity in oral environment as well as adverse effects and safety consideration.

This invention is directed to a novel method of using a therapeutic composition comprising a compound of an α-ketoalkanoic acid salt (pyruvate) and/or its derivatives for the treatment of hydrogen peroxide ($H_2O_2$) mediated/induced local inflammation on the tooth structure, surrounding supporting ligaments and oral soft tissue (gingiva and mucosa), during and after external tooth whitening procedure.

The compound is a α-ketoalkanoic acid salt, a physiologically acceptable salt of a α-ketoalkanoic acid, an ester of a α-ketoalkanoic acid salt, or an amide of a α-ketoalkanoic salt. Salts of a α-ketoalkanoic acid, not the free acid, are preferred.

Current Status and Problems of Dental Whitening Procedures Based On $H_2O_2$ or Related Oxy Radicals Exogenous Hydrogen Peroxide is known to cause irritation to many different tissues such as the skin, eyes, esophagus and stomach. Inadvertent exposure of oral soft tissues to a concentrated solution of $H_2O_2$ is known to cause extensive tissue damage in the form of vesicle formation and ulceration.

Dental whitening agents such as Hydrogen Peroxide ($H_2O_2$) and related oxiradicals such as Carbamide Peroxide (CP) and various other Peroxo-Adducts of inorganic anions are widely used for the bleaching of discolored teeth, both in a professional dental office setting as well as for personal use in additives to oral gels and oral rinsing solutions.

Many studies have examined the mechanisms of action of these and related products, focusing on potential oxidative stress and redox activity in the oral environment as well as possible adverse effects and safety concerns.

One in vitro study showed that $H_2O_2$ could penetrate dental enamel, dentine and reach even the pulp chamber.

Furthermore, it has been shown that $H_2O_2$, by creating an acidic environment, alters and removes the protective "smear" layer of the dentin as one of the contributing factors to compromise cellular functions.

There is accumulating evidences supporting a direct link between mitochondria which play a key role in energy yielding metabolism and also cell death, the latter as a result of oxidative stress by ROS including $H_2O_2$.

Also mucosal tissue safety concerns relate to the potential cytotoxic effects of free radicals produced by the peroxides used in bleaching products: interactions with proteins, lipids and RNA and DNA can lead to cellular damage resulting in apoptosis or direct cytolysis.

Commonly voiced complaints by patients when treated with bleaching agents at commercially available concentrations are considerable tooth sensitivity, discomfort or even direct pain.

Using Carbamide Peroxide, up to 65% of patients report discomfort; when a thermal procedure is added to enhance the bleaching effect, the percentage of patients complaining of pain increases to 91%.

There are isolated reports of patients who have developed oral ulcerations after using 3 percent hydrogen peroxide for 1-2 minutes, 3-5 times daily, while at lower concentrations, changes are less marked or inconspicuous even with continuous exposure.

No effective treatment is yet known or in development to mitigate or perhaps abolish the discomfort and pain of current teeth whitening techniques and procedures.

The most often method to alleviate post-tooth-whitening sensitivity, offered in every professional tooth whitening kit, is the use of fluoride in the affected local area.

Although fluoridated applications are generally effective, the relief of discomfort and sensitivity is not immediate, as it will take weeks to become effective; this delayed effect is probably due to the slow apposition of the fluoridated compounds in the openings of the dentinal tubules.

Bleaching Gels create a high osmotic gradient, given their osmolarity is 17 to 190 times higher than the osmolarity of the dentinal tubular fluid. This creates an osmotic gradient for and out flux of the dentinal tubular fluid resulting in pain (tooth sensitivity) felt by the patient.

As peroxide decomposes, in addition to the formation of molecular oxygen, oxygen ions and radicals ($O_2^-$) protons are released. This process can change initially neutral gel to an acidic gel with a pH as low as 3.

The more acidic and the more anhydrous the bleaching gel becomes, the stronger the osmotic gradient pull, and the more forceful is the outflow within the tubule.

It is this outflow of dentinal fluid that is generally assumed to cause an acute discomfort (tooth sensitivity) for the patient.

The relative sensitivities of pulpal, gingival and periodontal ligament cells to toxic effects of hydrogen peroxide are important given the potential for diffusion of hydrogen peroxide through dentine, and thus resulting in pain.

Indeed recent studies have demonstrated that dental bleaching depends on the penetration of hydrogen peroxide ($H_2O_2$)-derived free radicals through enamel and into dentin, fragmenting dentin's chromogenic molecules into smaller components.

Previous observations have confirmed that interactions between teeth dentine and bleaching agents involve diffusion and reaction of $H_2O_2$ moieties with chromogens (120), so that a direct correlation between the presence of oxidative agents and the penetration potential of $H_2O_2$ has already been demonstrated Considering the fact that enamel permeability for $H_2O_2$ is limited and the organic content is about 2%, the most susceptible area of the tooth for $H_2O_2$ interaction with organic compounds is at the DentinoEnamel Junction, where the strong oxidizing ability of $H_2O_2$ is responsible for the loss of structural organic components.

The reaction between $H_2O_2$ and dentin's inorganic compounds could result in the formation of harmful acid byproducts such as hydrogen phosphate These $H_2O_2$-induced changes in the organic and inorganic matrix of dentin are considered to be responsible for the inflammatory changes and possible long-term pulpal damage.

Furthermore the role of ROS in the etiology of $H_2O_2$-induced tooth sensitivity should be appreciated not be ignored. It has been concluded that, as a result of high concentration hydrogen peroxide employed in external tooth bleaching, an increase of ROS and increase in the activity of the proteolytic enzyme (lysosomal, catepsin B) occurs inside the pulp chamber.

Non-Dental Applications of Alpha-Keto Carboxylates, Particularly Pyruvate, as Oxygen Radical Scavenger and Antioxidant Pyruvate is a glycolytic metabolite with unique antioxidant, NADH-redox, and energetic features in mammalian cellular systems.

It is a natural α-ketocarboxylate that is also an effective scavenger of reactive oxygen species (oxygen radical scavenger, ROS) with virtually no or little cytotoxicity when applied exogenously in concentrations up to about 10 mM (one hundred fold its physiological level) in short term studies.

Pyruvate-treated human and bovine endothelial cells subjected to a 30 min pulse of oxidative stress by 0.5 mM hydrogen peroxide ($H_2O_2$) showed that pyruvate dose-dependently enhanced cellular viability and survival, increasing the bcl-2/bax ratio and stabilizing the cellular glutathione pool.

In isolated liver mitochondria subjected to oxidative stress by simulated ischemia/reperfusion 1 mM pyruvate stabilized respiration, prevented the dissociation of cytochrome C, and enhanced expression of antiapoptotic bcl-2.

In the $H_2O_2$-treated endothelial cells pyruvate also transiently increased phosphorylation of ERK1/2 (anti-apoptosis) and prevented the accumulation of phosphorylated p38 mitogen activated kinase (pro-apoptosis).

In L-lactate which generates cytosolic free NADH relative to pyruvate treatment.

These observations point to a redox-related mechanism of action of anti-apoptotic pyruvate.

Enhanced mitochondrial respiration coupled with enhanced bcl-2- and cytochrome C-retention in the isolated liver mitochondria treated with pyruvate indicated improved mitochondrial (inner) membrane stability, enabling improved energetic function and mitochondrial membrane potential Δφ.

Thus, the cytoprotective mechanism of antioxidant pyruvate is multifactorial, involving cytosolic and mitochondrial redox systems, enhanced survival signaling, and improved mitochondrial inner membrane function.

Pyruvate is also well-documented to strengthen the first line of cellular defense against oxidative stress by increasing the cytosolic $NADPH/NADP^+$ ratio along with an increase in the GSH/GSSG ratio.

In whole organ systems and animal preparations pyruvate has been shown to inhibit myocardial stunning, reduce myocardial infarct size, prolong cortical function during prolonged ischemia, attenuate LPS-induced sepsis.

Pyruvate has also displayed features of metabolic positive inotropy, as in 1-10 millimolar concentrations it not only increases mitochondrial stability and mitochondrial Δφ but also improves the calcium transients of isolated cardiomyocytes consistent with improved cardiac contractility without apparent cytotoxicity.

Pyruvate as an Endogenous Anti-Inflammatory Agent (Except for Subheadings and References, Passages are Transcribed From R. Bünger Et Al.

A) Physiological and Pathological Generation of Oxiradicals:

ROS such as superoxide anions, hydrogen peroxide, and peroxynitrite are naturally formed in conditions of high cytosolic (and possibly mitochondrial) NADH redox potentials (high free $[NADH]/[NAD^+]$ ratio) in the presence of molecular oxygen and, nitric oxide (NO).

It has been estimated that normally up to 2% of mitochondrial oxygen uptake results in formation of ROS (superoxide radical and hydrogen peroxide) via complex I and/or complex III of the mitochondrial respiration chain.

Increased cellular levels of ROS have been implicated in tissue injury due to, e.g., ischemia/reperfusion or hemorrhage/resuscitation, possibly mediated in part via NAD(P)H-dependent membrane-bound NAD(P)H oxidases that generate the superoxide radical.

ROS have also been, found, to alter signaling pathways by oxidizing reactive cysteine residues in specific proteins, reversibly inactivating tyrosine phosphatases and other proteins.

Such protein thiols and sulfhydryl groups after being mildly oxidized by ROS may be re-reduced by reduced glutathione (GSH), one of the most abundant natural cellular antioxidants, whereas continued high levels of oxidative stress probably cause irreversible oxidation of the cysteine thiols and loss of biological activity of peptides and proteins.

B) Pyruvate's Central Role in Intermediary Energy and Redox Metabolism:

Pyruvate is a natural three-carbon glycolytic intermediate with a number of special attributes that are effectively interacting with the redox and energy metabolism of the cell.

Besides its central role in amino acid metabolism, it is substrate and allosteric activator of the mitochondrial pyruvate dehydrogenase and of the $CO_2$-fixing mitochondrial carboxylase, which renders pyruvate the anaplerotic precursor of mitochondrial oxaloacetate and citrate providing substrate for the NADPH-dependent isocitrate dehydrogenase (ICDH) and maintaining the level of citric acid cycle intermediates.

With respect to the redox systems in the cytosol, pyruvate is the precursor of L-lactate via the abundant near-equilibrium lactate dehydrogenase, a reaction that produces cytosolic free $NAD^+$ thus effectively competing for NADH substrate for superoxide generating NAD(P)H oxidases.

This only recently recognized feature identifies pyruvate as a natural antioxidant that additionally stabilizes the cellular ATP pool and can raise the cytosolic phosphorylation potential substantially.

C) Pyruvate as Oxiradical Scavenger:

Pyruvate is also a very effective non-enzymatic scavenger of intra- and extracellular oxyradicals such as hydrogen peroxide and particularly of peroxynitrite (rate constant 88-100 $mol^{-1}*s^{-1}$ at pH 7.4, 37° C.,), an especially cytotoxic oxyradical.

In the reaction between pyruvate and peroxynitrite pyruvate decarboxylates to acetate at a speed that is about one order of magnitude faster than that with $H_2O_2$; peroxynitrite itself can be formed extremely fast from NO and the superoxide anion with a rate constant of $4-7*10^9$/mol*sec.

D) Pyruvate as Natural Cytoprotective Antioxidant Molecule:

Antioxidant pyruvate has been found strikingly effective and beneficial in numerous experimental and some short-term clinical pilot studies, with little or no detectable toxicity.

For example pyruvate is cytoprotective in ischemia/reperfusion or infarct/stunning paradigms in tissues such as heart, brain, kidney, liver, lens, vascular endothelium, and intestine.

The first published pilot study in heart failure patients with dilated cardiomyopathy also demonstrated beneficial efficacy of intracoronary pyruvate with no obvious toxicity.

Similarly, pyruvate cardioplegia reduced mortality and morbidity in a recent study on elective coronary revascularization in cardiac patients as well as in in-vitro perfused hearts.

E) Mechanisms of Pyruvate Cytoprotection:

The pyruvate protective mechanisms are likely multifactorial, mediated by improved cellular NADH- and thiol redox status alone or combined with enhanced mitochondrial anaplerosis and energetics. Pyruvate treatment inhibits the basal and the reperfusion burst of ROS, decreases cytosolic free NADH levels and thus NAD(P)H oxidase activity, preserves or increases the cytosolic NADPH and GSH pools, stabilizes cellular ATP and hence intracellular pH, raises the thermodynamic ATP phosphorylation potential, and prevents the mitochondrial permeability transition in reperfusion following cardiac ischemia.

There is another less-well recognized antioxidant mechanism of pyruvate which is mediated by the anaplerotic mitochondrial pyruvate carboxylase; in this pathway pyruvate stimulates formation of matrix oxaloacetate and citrate; the latter, after export into the cytosol, can exert two major effects with respect to the cellular antioxidant status: i) allosteric inhibition of the phosphofructokinase causing upstream accumulation of glucose-6-phosphate and thus enhanced potential for oxidative pentose phosphate pathway (PPP) flux required for reductive syntheses and reduction of cytosolic NADP and oxidized glutathione (GSSG) to NADPH and GSH, respectively; ii) direct stimulation of the NADPH-dependent isocitrate dehydrogenase of the cytosol which also yields NADPH available for reduction of GSSG.

III. SUMMARY OF THE INVENTION

It is the objective of this invention i) to provide an acceptable pharmaceutical composition, with the active ingredient as Pyruvate or related α-keto carboxylates, as novel adjuvants in the treatment of post-tooth-whitening sensitivity and ii) to take advantage of the cytoprotective efficacy of pyruvate in oral soft tissue after application of an external high-concentration-$H_2O_2$ insult. Two therapeutic solutions are recommended: 1) A Standard solution, at about five times isotonic concentration, with a 750 mM sodium pyruvate; this solution contains 250 mg sodium pyruvate in a 3 ml solution, recommended for the general purpose of neutralizing hydrogen peroxide post intraoral tooth whitening process; 2) An Emergency solution, extremely hypertonic at 3.3 M (1.2 g of sodium pyruvate in a 3 ml solution, recommended for treatment of painful gingival inflammation with exudate.

IV. DETAILED DESCRIPTION OF THE INVENTION

Novel Dental Applications of Pyruvate and Related Alpha Keto Carboxylates

As a scavenger of $H_2O_2$ and related ROS during and after the process of tooth whitening As an oxidizing redox metabolite: Increased $NAD^+$/NADH ratio, inhibition of NADHoxidase and hence inhibition of formation of superoxide radical and likely release of inflammatory cytokines, and pyruvate also strengthens the reductive power of the glutathione system, the first line of defense against oxidative stress.

These two principal effects of pyruvate suggest it could be beneficial in $H_2O_2$-based tooth whitening procedures by ameliorating or perhaps even abolishing discomfort and pain of the procedure Although deleterious tooth sensitivity is a common side effect of external tooth whitening of otherwise healthy teeth, the etiology is poorly understood.

It is known that dentin hypersensitivity primarily results from the exposure to $H_2O_2$ in presence of open dentinal tubules.

This hydrodynamic theory of dentin hypersensitivity is generally accepted: any thermal, tactile, osmotic, or chemical stimuli will likely cause the deformation or irritation of nerve endings at the Raschkow plexus; this stimulates transmission and pain sensation.

The most sensitive area of the tooth is located at or near the DEL (dentino enamel junction with a large number of open dentinal tubuli; therefore it is this area that is considered the primary locus of tooth sensitivity and pain sensation.

This invention is directed at a method of ameliorating the harmful Tooth-Sensitivity effects of $H_2O_2$-containing, commercially and professionally Tooth-Whitening Product employing pyruvate anion as the active ingredient.

One aspect the invention prevents the $H_2O_2$ toxicity by pyruvate's feature to non-enzymatically interact with hydrogen peroxide ($H_2O_2$) and possibly also other peroxides such as carbamide peroxide (CP) and peroxo-adducts of inorganic anions such as peroxoborate, peroxodisulphate and peroxocarbonate, all agents for the bleaching of discolored teeth in professional and commercially-available tooth-whitening products such as gels, toothpastes and oral rinses In the case of $H_2O_2$, the latter reduced to $H_2O_2$ and pyruvate is decarboxylated to carbon dioxide ($CO_2$) and acetate.

The second aspect of the invention relates to the cytoprotective aspect of the α-keto acids, such as pyruvate, via its ability to increase the reductive power of the glutathione system, the first line of cellular defense against oxidative stress, most likely through the pentose phosphate (or hexose-monophosphate) and isocitrate dehydrogenase pathways.

Furthermore, pyruvate is a natural redox metabolite in the cytosol which tends to produce mild intracellular alkalization, simultaneously oxidizing free NADH thereby limiting the activity of the NADH oxidase, the ubiquitous enzymatic activity that generates the superoxide anion, ($O_2^-$) that combined with the NO, will generate peroxynitrite, a highly cytotoxic compound.

Thus, pyruvate, besides its central role in intermediary metabolism, also functions as a natural endogenous antioxidant.

One key feature of pyruvate is its ability to directly neutralize hydrogen peroxide on a 1 to 1 molar basis.

Under cellular conditions this interaction is spontaneous and does not require enzyme catalysis; it is an interaction between pyruvate's carbonyl group (α-keto group) and hydrogen peroxide yielding carbon dioxide and acetate.

This reaction is probably enhanced by the presence of free $Fe^{2+}$ (ferrous ion).

The released carbon dioxide is highly diffusible across cellular membranes and any excess can effectively be removed from cells and organs via the lung.

Acetate, the product of the $H_2O_2$-induced pyruvate-decarboxylation, can be readily metabolized by the mitochondrial acyl-coenzyme A synthase generating acetyl-CoA, which readily enters and can stimulate the citric acid cycle turnover rate.

The non-enzymatic decarboxylation of pyruvate by $H_2O_2$, combined with pyruvate-induced metabolic enhancements of the NADH- and NADPH/GSH systems plus the known improvement of the cellular energy status, are considered the key mechanisms to alleviate sudden oxidative stress (e.g., ischemia'reperfusion, hypoxic perfusion, metabolic acidosis, iron overload and other types of related).

These beneficial effects of pyruvate require pyruvate levels ≥0.5 mM, with optimum efficacy at 2-5 mM.

Physiological pyruvate levels are substantially lower, varying between 50-200 microM. Applying this mechanism to dental tooth whitening, a given spike in the extracellular concentration of $H_2O_2$ in the crevicular fluid that surrounds the dentinal tubules would reduce available pyruvate, but simultaneously reduce overall oxidative stress via its multifactorial beneficial effects.

Any exposure of cells to exogenous $H_2O_2 \geq 100$ microM inflicts oxidative stress and is cytotoxic, as a result of $H_2O_2$'s direct action on cell membranes and subcellular structures, as well as through the formation of other cytotoxic KOS species (superoxide anion, hydroxyl radical). It is known that superoxide anions alone are not highly reactive, but these ROS becomes highly toxic when reacting with nitric oxide (NO), forming the highly cytotoxic peroxynitrite, a particularly reactive oxidant ROS.

Interestingly, as the physiological pyruvate anion reacts about 40 times faster with peroxynitrite than with $H_2O_2$, pyruvate (as well as its ethanol ester ethyl pyruvate) will likely be cytoprotective against peroxynitrite; this protective effect is already seen at high physiological/or low pathological pyruvate levels≥0.5 mM, values which have been reported for plasma as well as intracellular and intramitochondrial compartments.

Pyruvate and other α-ketoacid salts, because they react rapidly, stoichiometrically, and nonenzymatically with $H_2O_2$ protect cells from programmed cell death (apoptosis) and cytolysis.

Pyruvate anion can also modulate favorably the cellular hydrogen ion balance.

This is the case, because under steady state conditions, therapeutically applied pyruvate, although it is imported by a proton-symport mechanism, stimulates metabolically hydrogen ion removal intracellularly, by metabolic sequestration (via mass-action effects) as opposed to direct chemical buffering mediated by, e.g. bicarbonate or synthetic cellular buffers.

Therapeutic Pyruvate can temporarily transform the cytoplasmic environment into a "proton sink" by increasing the levels of $NAD^+$ leading to substantial accumulation of reduced metabolites such as L-lactate or oxaloacetate.

Thus the exogenously applied pyruvate anion can indirectly function as natural intracellular hydrogen ion buffer, gently alkalinizing cells and blood without depending on extracellular buffers like bicarbonate and other synthetic buffers.

Taken together, these mechanisms and observations strongly support our hypothesis that pyruvate and/or its derivatives may have therapeutic potential as protectors against tooth sensitivity, especially when the latter is triggered by an excess $H_2O_2$ that unintentionally comes in contact with the oral mucosa and/or gingival, periodontal ligament and dentinal tubules.

Proposed Composition of Pyruvate

The current therapeutic composition of the invention employs the sodium salt of pyruvate in its keto configuration (not the tautomeric enol form), synonym: α-Ketopropionic acid-2, 3-13C2 sodium salt; molecular weight is 110.

The active ingredient is the organic pyruvate anion in presence of the $Na^+$ cation, given the high water solubility and relative stability of this salt (R. Bünger et al., unpublished observations) and the prevalence of the keto tautomer in aqueous environments.

As for the application modes, the therapeutic compositions of the invention may be administered topically (e.g. ointment, gels or cream), by routine methods in pharmaceutically acceptable inert carrier substances, where the prolonged contact (slow release preparation) with the oral tissue is a key element.

For example, the therapeutic compositions of the invention may be administered in a sustained release formulation using a biodegradable biocompatible mucoadhesive polymer.

It is known that, in aqueous solution at room temperature, free pyruvate acid may undergo hydration and formation of geminal diol of pyruvic acid, 2,2-dihydroxypropanoic acid.

Minimization of the enol tautomeric configuration in the present therapeutic composition requires the use of the sodium salt as well as on site preparation of the therapeutic composition of the active ingredient (sodium pyruvate).

The main component of the pharmaceutically acceptable carrier should be a biocompatible mucoadhesive polymer.

In the case of intense tooth sensitivity caused by the whitening agent $H_2O_2$, the pharmaceutical composition of this invention will be selectively applied around the gingival margin, gingival sulcus, and the dentino enamel junction.

The presence of the biodegradable, biocompatible mucoadhesive polymer, in the pharmaceutical composition, will assure a prolonged contact of the active ingredient (sodium pyruvate) with the affected area of the tooth, the dentino enamel junction, gingival sulcus, and the keratinized and non keratinized gingiva surrounding the tooth.

Based on this mucoadhesive property of the biocompatible polymer, the active ingredient is assured to be delivered locally to the affected site, neutralizing the presence of the $H_2O_2$ and likely strengthening the cellular local antioxidant defenses, without being diluted, or washed away by the oral fluids or saliva, thus increasing the effectiveness as a local protector against teeth discomfort.

The same method of delivering the active ingredient will be performed for areas of soft tissue of the oral mucosa, that inadvertently came in contact with high concentrations of $H_2O_2$ used in the process of tooth whitening, thus likely neutralizing the toxicity of $H_2O_2$ and minimizing tissue damage.

Clinical Application

The present therapeutic formulation of this invention contains the active ingredient (sodium pyruvate) at 5 mmol (550 mg)

pH of the formulation 6-8.

Pharmaceutically acceptable carrier
Mucoadhesive polymer
Device.

Two individual plastic syringes.

One containing the active ingredient, sodium pyruvate, in a dry, crystalline form.

The second syringe containing the pharmacological carrier, mucoadhesive polymer in a gel form.

Before the application of the pharmacological composition, the two syringes will interlock at the opposite ends and the two components will be pushed (by depressing the plunger) back and forth until complete homogenization has occurred and the gel is consistent throughout the syringe.

Twist to separate the two syringes and attach the brushed applicator tip onto the base syringe.

Apply at the affected site.

Supporting Preliminary Data

Preliminary data collected during professional tooth whitening in the dental practice setting of Dr. Zoltan Rusznak, Ashburn, Va., support the efficacy of sodium pyruvate post treatment The preliminary results are unpublished data, suggesting that the proposed sodium pyruvate salt preparation can indeed eliminate tooth sensitivity and deleterious tooth sensitivity post treatment.

Materials and Methods

In-office laser tooth whitening procedure using Biolase EZ lase, 7W diode laser, and the LaserWhite *20 whitening gel kit.

A total of 15 candidates were selected and screened (for the presence of active decay, faulty restorations, cervical abrasion and attrition, enamel cracks) for the whitening procedure.

The arch has been divided in 4 quadrants, K1 (upper right), K2 (upper left), K3 (lower left), K4 (lower right).

The amount of 400 Jules has been applied per quadrant per application, in two separate applications. (total of 800 Jules per quadrant).

The candidates were assigned to 3 groups.

Group 1 is considered the control (C1), receiving desensitizer (post treatment) containing potassium nitrate.

Group 2, a second control group (C2), received as desensitizer (post treatment) stannous fluoride.

Group 3 (C3) received as desensitizer sodium pyruvate 99% in crystalline form. (applied over the gingival, gingival margin and DEJ).

Discussion

During the procedure tooth sensitivity has been observed in 2 of the subjects in each group, localized at K3, and K4.

At the end of the whitening procedure control group C1 experienced tooth sensitivity, (3 out of 5 subjects) even after the application of the desensitizer, lasting up to 24 hours, confirmed by follow up phone calls.

Control Group C2 experienced tooth sensitivity, 100% of the members, lasting over 24 hours confirmed by follow up phone calls to the subjects.

Group C3 experienced tooth sensitivity, (1 of 5 subjects) after the application of sodium pyruvate, but no subject reported extended sensitivity over 24 hours.

In addition, overall 6 patients presented with gingival lesions, manifested by burning sensation on the gingival margin, and visually expressed by white areas on the gingival margin.

These patients when treated only with sodium pyruvate, reported an immediate relieve of the burning sensation.

Visual inspection confirmed a normal appearance of the gingiva at the previously discolored site.

These preliminary data suggest that the sodium salt of pyruvate is highly effective in post-tooth-whitening procedures, by reducing and/or completely eliminating tooth sensitivity and pain.

In addition the findings suggest that the sodium salt of pyruvate is highly protective in soft oral tissue damaged by inadvertently spilled $H_2O_2$ used during tooth whitening procedures.

The invention claimed is:

1. A method of whitening teeth, comprising:
    applying a teeth whitening solution to the teeth of a person, wherein the teeth whitening solution comprises hydrogen peroxide;
    preparing a pharmaceutical composition by mixing sodium pyruvate with a preparation comprising a mucoadhesive polymer and a pharmaceutically acceptable carrier for the mucoadhesive polymer;
    applying the pharmaceutical composition to the teeth and mouth of the person;
    allowing the pharmaceutical composition to reside on the teeth and mouth of the person for a period time from 30 seconds to 10 minutes; and
    rinsing the teeth and the mouth of the person with water.

2. The method of claim 1, wherein the sodium pyruvate is in a first container and the preparation is in a second container and the mixing is performed by moving the contents of the first container into the second container and then moving the contents of the second container into the first container.

3. The method of claim 1, wherein the pharmaceutical composition is allowed to reside on the teeth and mouth of the person for a period time from 2 minutes to 10 minutes prior to rinsing.

4. The method of claim 2, wherein the sodium pyruvate is in a concentration range between 750 mM (millimol/l) and 3.3M (mol/l), and any concentration in between the specified range.

* * * * *